(12) United States Patent
Gardner et al.

(10) Patent No.: US 8,470,537 B2
(45) Date of Patent: *Jun. 25, 2013

(54) SEQUENTIAL ADDITION OF SHORT DNA OLIGOS IN DNA-POLYMERASE-BASED SYNTHESIS REACTIONS

(75) Inventors: Shea N. Gardner, San Leandro, CA (US); Raymond P. Mariella, Jr., Danville, CA (US); Allen T. Christian, Tracy, CA (US); Jennifer A. Young, Berkeley, CA (US); David S. Clague, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/959,789

(22) Filed: Dec. 3, 2010

(65) Prior Publication Data

US 2011/0104763 A1    May 5, 2011

Related U.S. Application Data

(62) Division of application No. 10/727,779, filed on Dec. 3, 2003, now Pat. No. 7,871,799.

(51) Int. Cl.
  *C12Q 1/68*   (2006.01)
  *C12P 19/34*  (2006.01)
(52) U.S. Cl.
  USPC .................................. 435/6.12; 435/91.2

(58) Field of Classification Search
  None
  See application file for complete search history.

(56) References Cited

U.S. PATENT DOCUMENTS

| | | | |
|---|---|---|---|
| 6,375,903 B1 | 4/2002 | Cerrina et al. | |
| 6,537,776 B1 | 3/2003 | Short | |
| 7,871,799 B2 * | 1/2011 | Gardner et al. | 435/91.2 |
| 2003/0068643 A1 | 4/2003 | Brennan et al. | |
| 2003/0087238 A1 * | 5/2003 | Evans | 435/6 |
| 2005/0272042 A1 * | 12/2005 | Gardner et al. | 435/6 |

FOREIGN PATENT DOCUMENTS

| | | |
|---|---|---|
| WO | WO 02/30945 | 4/2002 |
| WO | WO 02/095073 A1 | 11/2002 |

* cited by examiner

*Primary Examiner* — Angela M Bertagna
(74) *Attorney, Agent, or Firm* — Eddie E. Scott

(57) ABSTRACT

A method of preselecting a multiplicity of DNA sequence segments that will comprise the DNA molecule of user-defined sequence, separating the DNA sequence segments temporally, and combining the multiplicity of DNA sequence segments with at least one polymerase enzyme wherein the multiplicity of DNA sequence segments join to produce the DNA molecule of user-defined sequence. Sequence segments may be of length n, where n is an odd integer. In one embodiment the length of desired hybridizing overlap is specified by the user and the sequences and the protocol for combining them are guided by computational (bioinformatics) predictions. In one embodiment sequence segments are combined from multiple reading frames to span the same region of a sequence, so that multiple desired hybridizations may occur with different overlap lengths.

1 Claim, 7 Drawing Sheets

US 8,470,537 B2

SEQUENTIAL ADDITION OF SHORT DNA OLIGOS IN DNA-POLYMERASE-BASED SYNTHESIS REACTIONS

CROSS-REFERENCE TO RELATED APPLICATIONS

This application is a Divisional of non provisional application Ser. No. 10/727,779, filed Dec. 3, 2003, entitled "Sequential Addition of Short DNA Oligos in DNA-Polymerase-Based Synthesis Reactions" (now U.S. Pat. No. 7,871,799) which is incorporated herein by this reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to DNA sequences and more particularly to constructing very long DNA sequences.

2. State of Technology

United States Patent Application No. 2003/0068643 by Thomas M. Brennan and Herbert L. Heyneker for methods and compositions for economically synthesizing and assembling long DNA sequences published Apr. 10, 2003 provides the following State of Technology information, "The advent of rapid sequencing technology has created large databases of DNA sequences containing useful genetic information. The remaining challenges are to find out what these genes really do, how they interact to regulate the whole organism, and ultimately how they may be manipulated to find utility in gene therapy, protein therapy, and diagnosis. The elucidation of the function of genes requires not only the knowledge of the wild type sequences, but also the availability of sequences containing designed variations in order to further the understanding of the roles various genes play in health and diseases. Mutagenesis is routinely conducted in the laboratory to create random or directed libraries of interesting sequence variations. However the ability to manipulate large segments of DNA to perform experiments on the functional effects of changes in DNA sequences has been limited by the enzymes available and their associated costs. For example, the researcher cannot easily control the specific addition or deletion of certain regions or sequences of DNA via traditional mutagenesis methods, and must resort to the selection of interesting DNA sequences from libraries containing genetic variations.

It would be most useful if a researcher could systematically synthesize large regions of DNA to determine the effect of differences in sequences upon the function of such regions. However, DNA synthesis using traditional methods is impractical because of the declining overall yield. For example, even with a yield of 99.5% per step in the phosphoramidite method of DNA synthesis, the total yield of a full-length sequence of 500 base pairs long would be less than 1%. Similarly, if one were to synthesize overlapping strands of, for example, an adenovirus useful as a gene therapy vector, the 50-70 kilobases of synthetic DNA required, even at a recent low price of approximately $1.00 per base, would cost over $50,000 per full sequence, far too expensive to be practical when compared with the enzymatic synthesis of DNA using PCR technology."

U.S. Pat. No. 6,375,903 issued Apr. 23, 2002 to Francesco Cerrina et al for a method and apparatus for synthesis of arrays of DNA probes provides the following State of Technology information, "The sequencing of deoxyribonucleic acid (DNA) is a fundamental tool of modern biology and is conventionally carried out in various ways, commonly by processes which separate DNA segments by electrophoresis . . . . One such alternative approach, utilizing an array of oligonucleotide probes synthesized by photolithographic techniques is described in Pease, et al., "Light-Generated Oligonucleotide Arrays for Rapid DNA Sequence Analysis," Proc. Natl. Acad. Sci. USA, Vol. 91, pp. 5022-5026, May 1994."

International Patent Application WO 02/095073 by Peter J. et al published Nov. 28, 2002 for a method for the synthesis of DNA sequences provides the following State of Technology information, "Using the techniques of recombinant DNA chemistry, it is now common for DNA sequences to be replicated and amplified from nature and for those sequences to then be disassembled into component parts which are then recombined or reassembled into new DNA sequences. While it is now both possible and common for short DNA sequences, referred to as oligonucleotides, to be directly synthesized from individual nucleosides, it has been thought to be generally impractical to directly construct large segments or assemblies of DNA sequences larger than about 400 base pairs. As a consequence, larger segments of DNA are generally constructed from component parts and segments which can be purchased, cloned or synthesized individually and then assembled into the DNA molecule desired."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a method of fabricating a DNA molecule of user-defined sequence, comprising the steps of preselecting a multiplicity of DNA sequence segments that will comprise the DNA molecule of user-defined sequence, separating the DNA sequence segments temporally, and combining the multiplicity of DNA sequence segments with at least one polymerase enzyme wherein the multiplicity of DNA sequence segments join to produce the DNA molecule of user-defined sequence. The method comprising preselecting a multiplicity of DNA sequence segments that will comprise the DNA molecule using computational techniques to break the user-defined sequence into fragments of defined size, arraying the fragments of defined size into groups, and assembling the groups into double-strand DNA molecules of predetermined base-pairs to produce the DNA molecule of user-defined sequence. In one embodiment the step of separating the DNA sequence segments temporally is accomplished by the DNA sequence segments being added gradually, in sequence order. In another embodiment the step of separating the DNA sequence segments temporally is accomplished by the DNA sequence segments being added gradually, in an order that is predicted computationally to minimize errors. In another embodiment a method of fabricating a DNA molecule of user-defined sequence comprises preselecting a multiplicity of DNA sequence segments that will comprise the DNA molecule of user-defined sequence, and combining the multiplicity of DNA sequence segments with at least one polymerase enzyme wherein the multiplicity of DNA sequence segments join to produce the DNA molecule of user-defined sequence.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
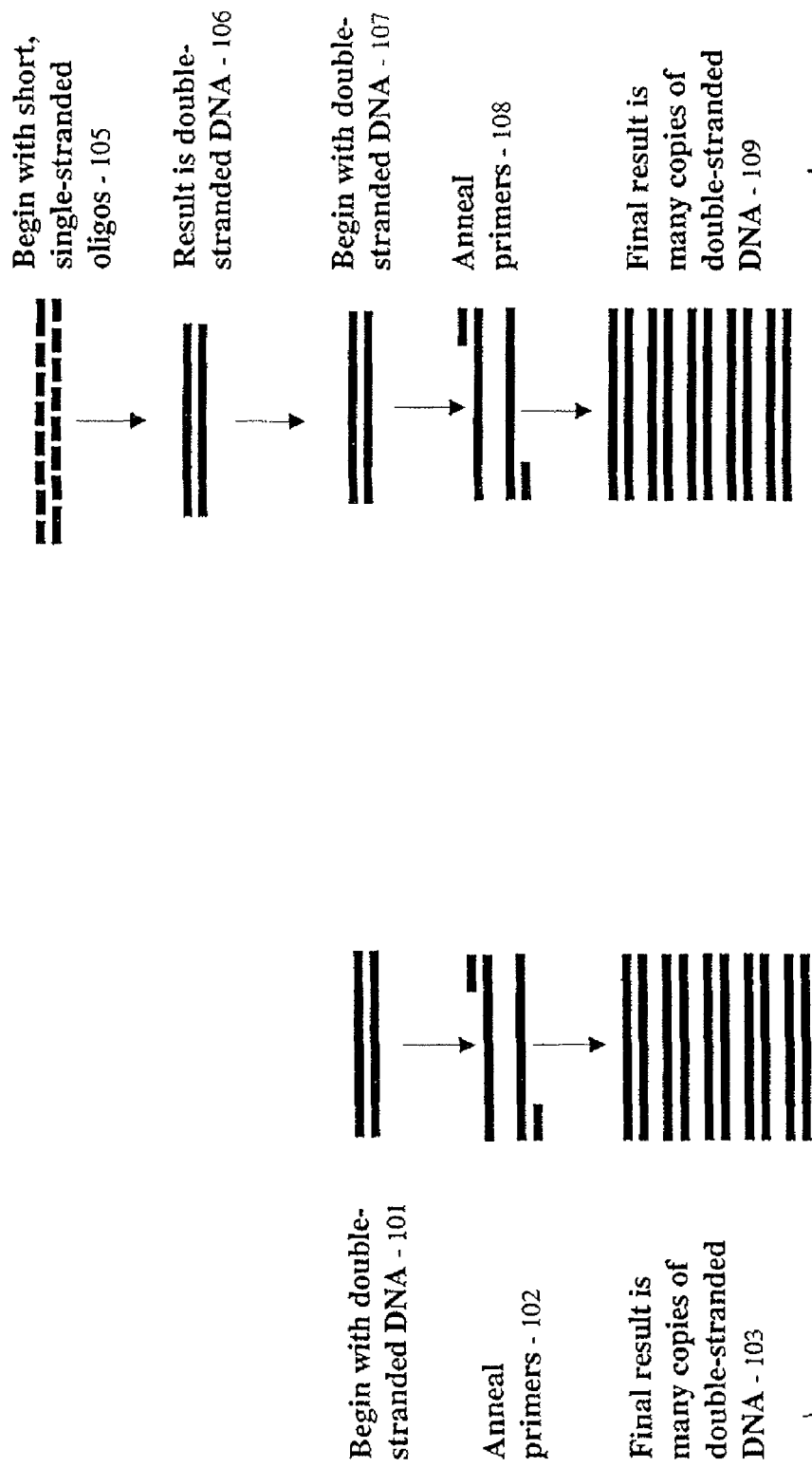
FIG. 1 is an illustration comparing conventional PCR and Polymerase-Based Synthesis.

Artificial gene synthesis is a widely used tool in molecular biology. Its utility is evidenced by, among other things, the gene synthesis services provided by more than a dozen companies worldwide. Uses include such common biological purposes as genes for transgenic studies, genetic engineering and mutagenesis, and uses as esoteric as encryption and DNA computing. The techniques for making synthetic genes are fundamentally understood; short oligonucleotides are made by phosphoramidite synthesis, and are then either joined together using DNA ligase, hybridized and extended using DNA polymerase, or created using various combinations of the two enzymatic approaches. The enzymatic processes themselves are relatively rapid and inexpensive; the factor that drives the cost and deliverable time of artificial genes is the need for phosphoramidite synthesis. A casual survey of gene synthesis service websites provides a cost per base of approximately $10.00 for genes longer than 2 kilobases; as the average gene is around 7000 bases, it is reasonable to expect to pay in the neighborhood of $70,000 to purchase an artificial gene. It is this cost, and the considerable delivery time, that has kept artificial genes from being as widely-used as they might otherwise be. DNA computing, for example, requires much more rapid turnaround; hours or days rather than weeks or months are necessary.

The two predominant factors in this price are labor and the price of the oligonucleotides. While both ligation and polymerase extension will work on oligos of a variety of lengths, 40 bases is the median length reported in the literature as starting substrates. Depending on the overlap necessary to assemble the oligos into a final product, a minimum of 350 oligos is required to make a 7000 base-pair gene. To synthesize the oligonucleotides required for this makes up an enormous fraction of the $70,000 estimated cost; the average market rate to buy these phosphoramidite-synthesized nucleotides is approximately $50,000. Clearly, a more cost-effective means of gene synthesis is called for, and preferably a synthesis method that permits more rapid delivery.

At the present time, the only way to synthesize nucleic acids de novo, without a template and starting from the component bases, is with phosphoramidite synthesis. Limitations on length, however, prohibit this method from being used to synthesize genes. While nucleic acids of up to 300 bases have been made, the practical limit is around 100 bases. Thus, phosphoramidite synthesis is used to produce de novo nucleic acids, and enzymatic techniques are then used to assemble these templates into a product of gene length. We reasoned, then, that to start with the shortest possible oligos would be the most economical means of producing gene-length DNA. To make a gene synthesis process truly economical, all of the components must be ready to hand; waiting for oligos to be synthesized and delivered represents a considerable part of the synthesis timeline. However, this requirement presents a considerable technical hurdle. To start with 40-base oligos requires that $4^{40}$ oligos be archived, which is clearly impossible. More plausibly, starting with 8-mers requires 65,536 oligos to represent every possible sequence, while 6-mers and 4-mers require 4096 and 256, respectively. Since all DNA synthesis methods require annealing single-stranded oligos, we avoided odd-numbered oligos to maintain consistency in the annealing process. A five-base oligo, for example, would have a 2-base overlap with one complement and a 3-base overlap with the second. Only 4 and 6-base oligos ("4-mers" and "6-mers") offered sufficient economic potential, so we concentrated on these as substrates for the synthesis method.

While DNA ligase works well to assemble oligos into longer products, ligases are limited as to the length of substrates upon which they can act; each has a "footprint" of precisely-defined size. (The extent of the physical overlap of the enzyme with its nucleic-acid substrate, as measured in number of base pairs, is referred to as its footprint.) As a survey of the literature produced no DNA ligases that could ligate either hexamers or 4-amers, we decided to use the polymerase extension method. Herein, we present results that demonstrate the viability of 4-base oligos as starting substrates for polymerase-based synthesis of functional genes.

The utility of synthetic long DNA and artificial genes is limited by the cost and time required to produce them. The cost factors involved are labor, the oligonucleotides that serve as building blocks for the final product, enzymes and sequencing verification. Of these, by far the most costly are time and the oligonucleotides templates.

The present invention comprises preselecting a multiplicity of DNA sequence segments that will comprise a DNA molecule of user-defined sequence, and combining the multiplicity of DNA sequence segments with at least one polymerase enzyme wherein the multiplicity of DNA sequence segments join to produce the DNA molecule of user-defined sequence. Descriptions of a number of embodiments of the present invention are provided. These descriptions serves to explain the principles of the invention. It is to be understood that the present invention covers all modifications, equivalents, and alternatives falling within the spirit and scope of the invention as defined by the claims.

In one embodiment of the present invention, Applicants have developed a technology that allows full-length, functional genes to be synthesized using 4-base oligonucleotides as templates, and proven polymerase-based primer extension technology. Only 256 4-mers are required to represent the entire spectrum of possible sequences; full-length genes can thus be made for less than $1000 in a matter of hours.

Referring now to the drawings, and in particular to FIG. 1, an illustration compares conventional PCR 100 and Polymerase-Based Synthesis 104. Conventional PCR 100 begins with doubled stranded DNA 101. The next step is to anneal primers 102. The final result is many copies of double-stranded DNA 103. Polymerase-Based Synthesis 104 begins with short, single-stranded oligos 105. This results in double-stranded DNA 107. The next step begins with doubled stranded DNA 107. The next step is to anneal primers 108. The final result is many copies of double-stranded DNA 109.

Figure 2:
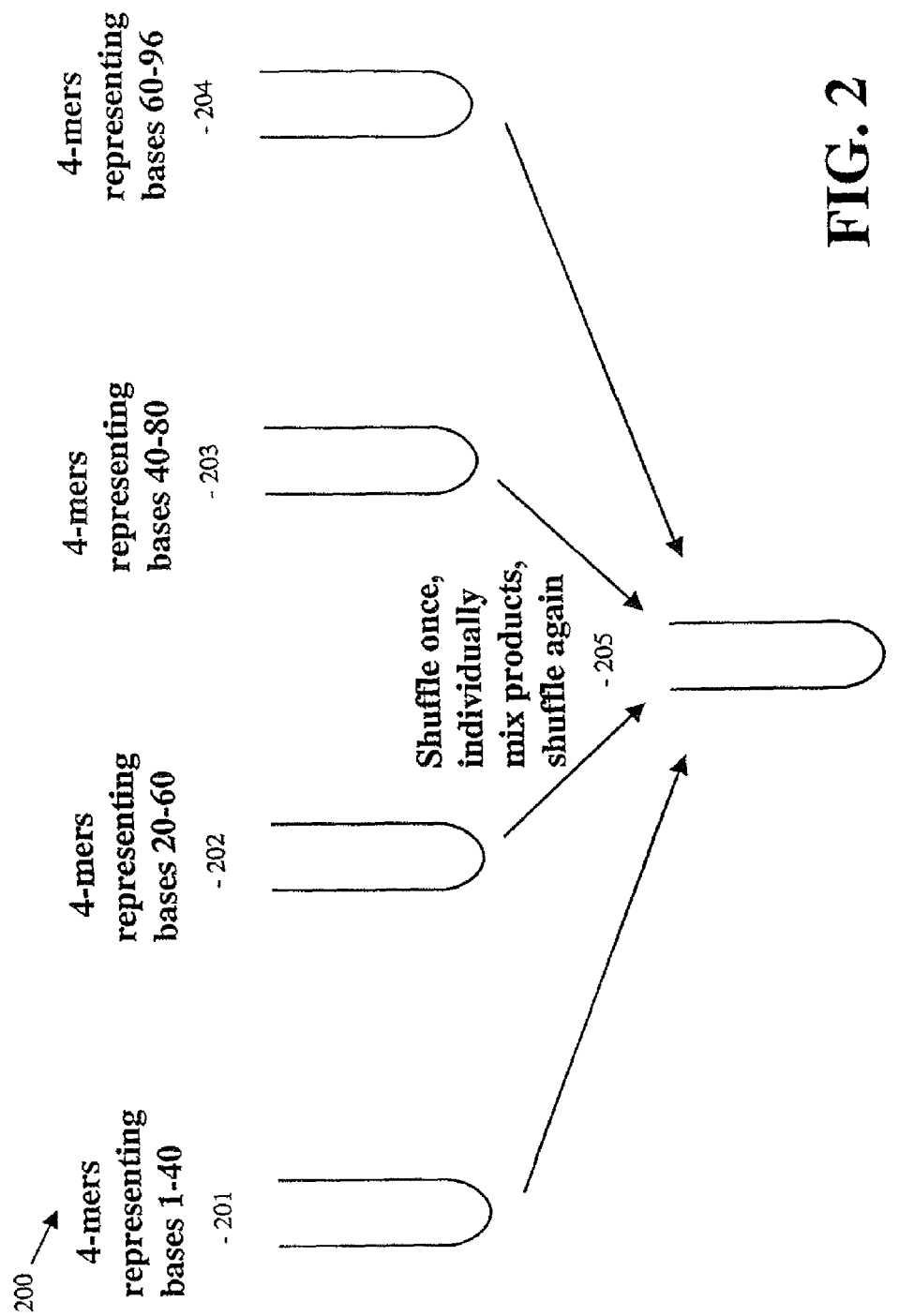
FIG. 2 is a schematic illustration of parallel synthesis.

Referring now to FIG. 2, one embodiment of the present invention is illustrated. A system of parallel synthesis assembly of a 100 base-pair molecule for 4-mer is designated generally by the reference numeral 200. This system of parallel synthesis 200 provides a process for making very long (greater than is possible with conventional phosphoramidite chemistry) DNA of user-defined sequence. The method begins by using computational techniques to break the desired sequence into fragments of defined size (e.g., 4 bases). These 4-base fragments are then arrayed in groups of approximately 20-40 4-base oligonucleotides (4-mers) and assembled into double-strand DNA molecules of 20-100 base-pairs using DNA polymerase. The products of these reactions are then combined, in as many steps as necessary, and assembled by polymerase into still-longer molecules, until the final desired product is assembled. The final product may then be amplified using PCR.

As illustrated by FIG. 2, the first embodiment system 200 of parallel synthesis provides assembly of a 100 Base-Pair Molecule from 4-mers. This illustration shows 4-mers representing bases 1-40 at 201, 4-mers representing bases 20-60 at 202, 4-mers representing bases 40-80 at 203, and 4-mers representing bases 60-96 at 204. The next step of the method is to use polymerase-based DNA synthesis once, individually mix products and to use polymerase-based synthesis again as illustrated at 205. The final product is show at 206.

This process allows the individual scientist to maintain all of the necessary reagents for DNA synthesis in storage. When a specific long DNA sequence is desired, they can be combined and assembled, as directed by the output of a computer program, by the individual researcher. This process allows rapid and inexpensive gene synthesis to be a widely available tool, rather than the custom product of large companies. These oligos can be synthesized by any of the many platforms extant; the sole requirements being that they are amenable to be copied and extended by DNA polymerases.

There are a variety of DNA polymerases that can be used for the synthesis PCR reactions. There are differences among them, and some are more appropriate for the assembly of 4-mers into ~40-base-pair molecules, while others work better for assembling the 40 base-pair molecules into longer molecules. Examples of appropriate DNA polymerases for this application include Vent®, or equivalent, and Deep Vent®, or equivalent, and Pfu®, or equivalent polymerase. Those that work best all have exonuclease capability to repair mismatches of DNA bases that occur either as a result of mis-hybridization, or of mistakes in the copying process.

This description of a first embodiment of the present invention illustrates a concept of using pre-made 4-mers to assemble long, user-defined DNA sequences. These can be purchased from any of many oligonucleotide synthesis companies, and are stored, frozen or lyophilized, until needed. The necessary 4-mers are selected based on the sequence of the desired product, and assembled.

The entire desired sequence is broken into 4-mers by a computer program, and then separated into small groups that can be made into double-stranded DNA molecules of 20-100 base-pairs. The products of these reactions are then grouped into secondary reactions, in which the short products from the first reactions are assembled into longer products. This process is repeated as needed, designed by the software, until the final product is assembled.

The assembly process is substantially the same as the process called DNA shuffling. It is similar to PCR in that there is a template, a primer, a DNA polymerase, and the attendant nucleotides and buffers. It is dissimilar to PCR in that the primer and template are the same entities—the 4-mers themselves. Following the parallel assembly process, the final product can be amplified by PCR. Any DNA polymerase commonly used for PCR can be used for this purpose.

Figure 3:
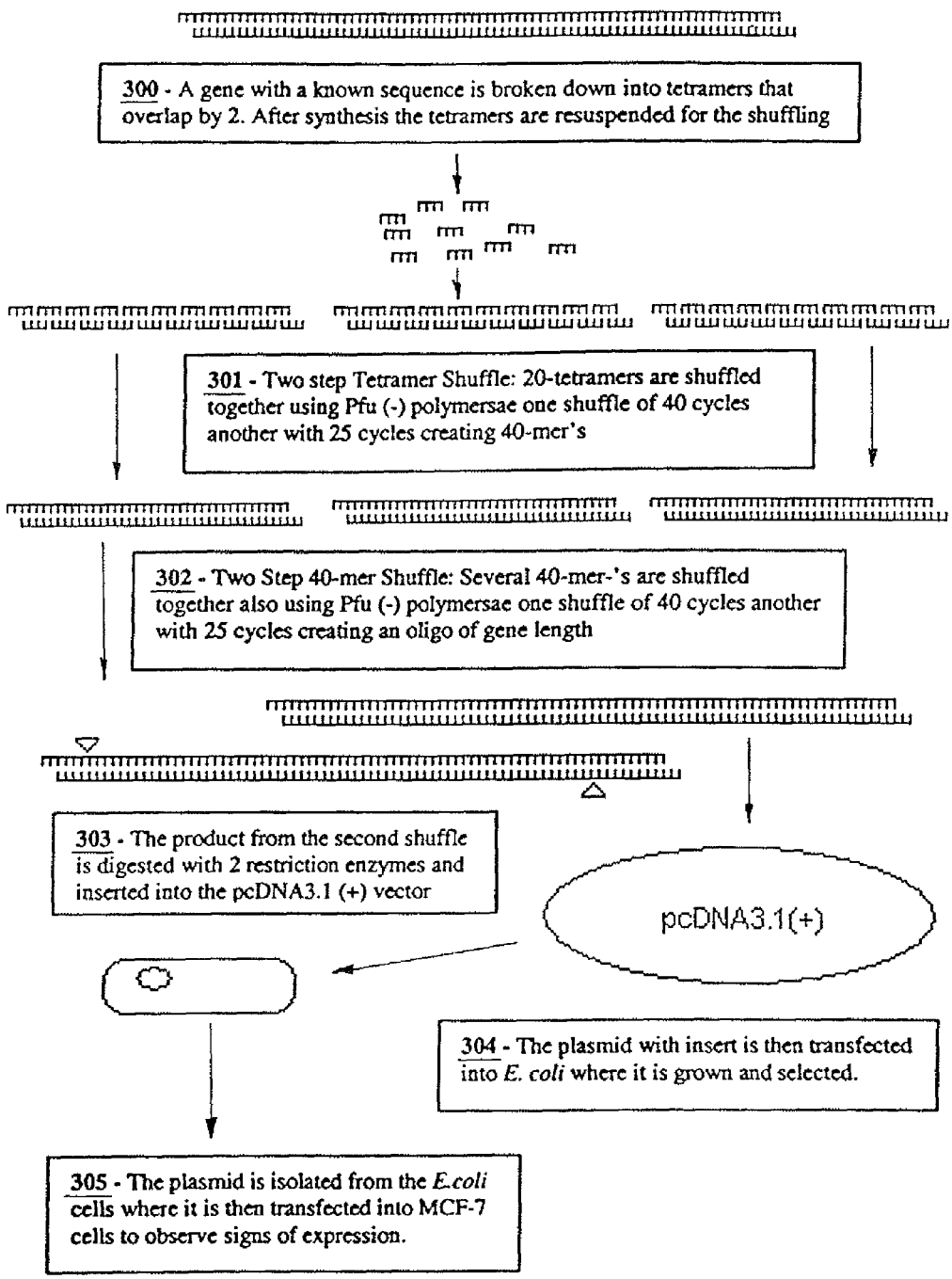
FIG. 3 is a schematic illustration of the assembly of a gene, Green Fluorescence Protein, and its cloning and functional expression in cells.

Referring now to FIG. 3, the system of parallel synthesis assembly of a 100 base-pair molecule for 4-mer is described in greater detail. This system of parallel synthesis provides a process for making very long (greater than is possible with conventional phosphoramidite chemistry) DNA of user-defined sequence. The method begins by using computational techniques to break the desired sequence into fragments of defined size (e.g., 4 bases). These 4-base fragments are then arrayed in groups of approximately 20-40 4-base oligonucleotides (4-mers) and assembled into double-strand DNA molecules of 20-100 base-pairs using DNA polymerase. The products of these reactions are then combined, in as many steps as necessary, and assembled by polymerase into still-longer molecules, until the final desired product is assembled. The final product is amplified using PCR.

In the first step 300, a gene with a known sequence is broken down into 4-mers that overlap by 2. After synthesis the 4-mers are resuspended for the shuffling. As shown at 301, in a two step 4-mer Polymerase-based DNA synthesis: 20-4-mers are reacted together via polymerase-based DNA synthesis using Pfu®, or equivalent, (−) polymerase, one reaction process of 40 cycles and another with 25 cycles, creating 40-mer's. In the next step 302, two Step 40-mer polymerase-based DNA synthesis: Several 40-mer-'s are reacted together also using Pfu®, or equivalent, (−) polymerase one polymerase-based DNA synthesis process of 40 cycles and another with 25 cycles, creating an oligo of gene length. As shown at 303, the product from the second polymerase-based DNA synthesis is digested with 2 restriction enzymes and inserted into the pcDNA3.1 (+) vector. As illustrated at 304, the plasmid with insert is then transfected into E. coli where it is grown and selected. In 305, the plasmid is isolated from the E. coli cells where it is then transfected into MCF-7 cells to observe signs of expression.

Applicants developed one embodiment of a method of fabricating a DNA molecule of user-defined sequence, comprising preselecting a multiplicity of DNA sequence segments that will comprise the DNA molecule of user-defined sequence by using computational techniques to break the user-defined sequence into fragments of defined size, arraying the fragments of defined size into groups, and assembling the groups into double-strand DNA molecules of predetermined base-pairs using DNA polymerase to produce the DNA molecule of user-defined sequence. Applicants made a number of observations in developing this embodiment. The observations include the following:

Functional Synthesis was the First Step—Applicants' first step was to be certain that they could perform the polymerase-based synthesis methods under conditions for similar chemical reaction that have been published in the literature. Applicants assembled a 1 kb segment of a plasmid using 100-mers as a substrate. These overlapped each other by 20 bases on either end; it took 13 100-mers to complete the sequence. Applicants then used 9 100-mers, also with a 20 base-pair overlap, to synthesize the mGFP sequence. Finally, Applicants used 36 40-mers, again with a 20 base-pair overlap, to assemble the same mGFP sequence.

Errors in Oligonucleotides Synthesis—It is important to note that phosphoramidite synthesis is not an error free process. Various types of errors inherent to the process have been described, the most common of which is failure to add a base at any given step. This is not a significant problem for many of the uses to which oligos are put, such as PCR, since only a fraction of the oligos in any given batch are likely to be affected.

Parallel Synthesis Versus Batch Synthesis: Rate and Accuracy—When performing the synthesis, reactions, one has the option of either combining all of the oligos and attempting the entire synthesis reaction in one step, or of assembling small fractions of the desired sequence in separate lots, and then combining the products for the final assembly process.

To Applicants' knowledge, no gene synthesis method is 100% accurate. Neither DNA ligase nor DNA polymerase has perfect fidelity, and errors in the process are bound to occur. Therefore, any product must be screened, preferably by sequencing. Beginning with 4-mers rather than 40-mers is certain to produce more failed and incorrect reaction products. Indeed, it comes as somewhat of a surprise that 4-mers are capable of annealing and producing any product at all.

Example Description—Applicants' goal was to synthesize a functional gene starting, preferably, with 4-mers. To accomplish this, Applicants naturally attempted many different technical approaches. Applicants chose a modified version of the Green Fluorescence Protein (mGFP) as their target gene, but in the course of developing the method Applicants synthesized various other things as well. The mGFP is 784 base pairs long; Applicants included an additional 30 bases on either end to serve as PCR primer site, and to aid in cloning the gene into a vector for functional expression.

GFP Gene Breakdown—The mGFP sequence obtained from NCBI was broken down into 616-4-(tetramer) base fragments, which overlap by 2 base pair (bp). The 4-mers synthesized by Genosys were resuspended with 10 mM Tris buffer to a final concentration of 300 mM. The 4-mers were mixed in 84 groups, which, with subsequent rounds of Polymerase Chain Reaction (PCR), created 776 base length products. All oligos were mixed in equal proportions and diluted to a 1:10 ratio.

Polymerase-based DNA synthesis with 4-mers—The resuspended oligos were combined in a PCR mixture containing 17.5 µL template 10 mM dNTP's, 2.5 µL Thermo Pol Buffer, 1 µLMgCl$_2$, and 0.6 µL Pfu®, or equivalent, (exo-) polymerase in 84 groups. No primers were added to this mixture. A PCR program with 40 cycles of 95° C. for 15 s, 40° C. for 30 s, and 72° C. for 10 s increasing by 1 s per cycle was run on this mixture on a MJ Research PTC-220 DNA Engine Dyad Peltier Thermal Cycler. The product from this reaction was then used as the template in a second reaction using the same mix as seen above. This mix was run on a PCR program with 35 cycles of 94° C. for 15 s, 40° C. for 30 s, and 72° C. for 45 s increasing by 1 s per cycle creating oligos from 8-30 bp in length.

Polymerase-based DNA synthesis with 8-30 mers—The products from the second PCR program were combined into 8 groups using 2 µL of each product mixed with 12.5 µL ddH$_2$O, 4 µL dNTP's, 2.5 µL Pfu®, or equivalent, (exo-) Buffer, 1 µLMgCl$_2$, and 0.6 µL Pfu®, or equivalent, (exo-) polymerase. The mixture was run on a PCR program of 40 cycles of 95° C. for 15 s, 40° C. for 30 s, and 72° C. for 10 s increasing by 1 s/cycle. Next, the reaction product was subjected to polymerase-based DNA synthesis, again, with the same amounts of dNTP's, MgCl$_2$, Buffer and Polymerase, but using 8 µL of the first product and 9.5 µL ddH$_2$O. This second mix was run for 25 cycles of 94° C. for 15 s, 40° C. for 30 s, and 72° C. for 45 s increasing by 1 s/cycle.

Polymerase-based DNA synthesis with 100 mers—The same process as above was repeated with the products of the second 8-30mer polymerase-based DNA synthesis. The product from the 8 groups was combined using 2 µL of each product mixed with 12.5 µL ddH$_2$O, 4 µL dNTP's, 2.5 µL Pfu®, or equivalent, (exo-) Buffer, 1 µLMgCl$_2$, and 0.6 µL Pfu®, or equivalent, (exo-) polymerase. Applicants use the same PCR programs as used above to create the gene length product.

PCR with Primers for 40 mer Product—1 µL of the final product was mixed with 25 µL dd H$_2$O, 5 µL each dNTP's, Thermosequenase Buffer, T7 primer, SP6 primer and Thermosequenase Polymerase. This mix was run at 95° C. for 5 min followed by 29 cycles of 94° C. for 1 min and 56° C. for 30 s ending with 3 min at 72° C.

Cloning and Transformation—The PCR product was digested with restriction enzymes (NheI and ApaI) and the fragment DNA purified from a 1.2% agarose gel. After ethanol precipitation, the DNA was dissolved in 2 uL 10 mM Tris pH 8.0. Restriction enzymes NheI and ApaI were also used to digest pcDNA3.1(+) vector (Invitrogen). Phenol-chloroform extraction and ethanol precipitation followed, and the DNA was brought to a volume of 5 uL in 10 mM Tris pH 8.0. The PCR product fragment and vector fragment were ligated with T4 DNA ligase. This assembled product was used to transform E. Coli Max Efficiency® DH5αF'IQ competent cells (Invitrogen), which were plated on LB/ampicillin plates and grown overnight. Bacterial colonies were picked and the plasmids purified using the Qiagen Plasmid Midi Kit.

Cell Culture and Transfection—MCF-7 (mammary gland adenocarcinoma) cells were cultured in DMEM/F12 supplemented with 5% fetal bovine serum (Gibco BRL), 2% 50×BME amino acids solution (Sigma), 1% MEM Non-essential amino acids solution (Gibco), 0.5 mM sodium pyruvate (Sigma), and 1 mM L-glutamine (Gibco). Twenty-four hours prior to transfection, cells were plated into six-well tissue culture dishes at 5×10$^4$ cells/well. For each well, cells were transfected with 4 µg plasmid DNA and 10 µl Lipofectamine™ 2000 reagent (Invitrogen Life Technologies) according to the manufacturer's recommendation. The plates were incubated at 37° C. in a 5% CO$_2$ atmosphere for 5 hrs, rinsed twice with antibiotic-free media (2 mL/well), and returned to the incubator. Twenty-four hours post-transfection, cells were subcultured at 100 cells per well. An additional twenty-four hours later, cells were replaced with selective growth medium containing 50 ug/mL ampicillin. GFP expression was visualized after three days using a Zeiss Axioskop fluorescent microscope with a filter for FITC.

Description of Another Embodiment—Applicants have previously described various embodiment of the invention comprising fabricating a DNA molecule of user-defined sequence by preselecting a multiplicity of DNA sequence segments that will comprise the DNA molecule of user-defined sequence, wherein the multiplicity of DNA sequence segments comprise n-mers, wherein n is a number less than 20, and combining the multiplicity of DNA sequence segments with at least one polymerase enzyme wherein the multiplicity of DNA sequence segments join to produce the DNA molecule of user-defined sequence. This embodiment provides an example of the polymerase-based synthesis of a user-defined DNA sequence, using pre-synthesized 8-base, single-stranded DNA molecules (8-mers) as starting substrates. For purposes of this example, when DNA is described as 40 bases long, it is presumed to be single-stranded. When DNA is described as being 40 base pairs, it is presumed to be double-stranded.

How a sequence is chosen: The DNA sequence is entirely user-defined. It can be a specific gene, human or otherwise, that one wishes to synthesize. It can also be a purely arbitrary DNA sequence, of any length. This DNA sequence will be made using very short oligonucleotides (synthetic single-stranded DNA molecules) and DNA polymerase.

Why a sequence is divided into short oligos: Once the sequence to be synthesized has been chosen, it is divided into 8-base segments, since these are the components from which the final product will be assembled. As the final DNA molecule will be double-stranded, for any given length of DNA, (e.g., 40 base pairs) the number of 8-mers necessary to synthesize it must be sufficient to produce a double-stranded molecule. Thus, rather than five 8-mers to make a 40-base-pair final product (8×5=40), the synthesis would require ten 8-mers. Once the desired molecule has been divided, the appropriate 8-mers can be gathered (from the possible 65,536 8-mers) for the subsequent polymerase-based assembly.

Why parallel synthesis is so important: There are literally billions of possible sequences resulting from combining the thousands of 8-mers necessary to make a gene-length product. If all of the component 8-mers were combined and reacted with DNA polymerase, the result would be a random collection of DNA, of innumerable different sequences, possibly none representing the correct one. It is therefore necessary to combine the component 8-mers into smaller groups, as this is the method most likely to minimize errors while producing the maximum amount of the correct product. The groups into which the 8-mers are divided will contain highly variable numbers of 8-mers; the size of each group is dependent on the initial sequence of the desired product. To make, for example, an 800-base-pair DNA molecule requires two hundred 8-mers. These may be combined in groups of any number from two to 200, depending on the sequence of the 800-base-pair product. The standard for the groups is ten 8-mers, or enough to produce a 40-base-pair DNA molecule.

How a sequence is divided into short oligos: The desired final sequence is divided into its component 8-mers by a computer program. This program uses the thermodynamic and kinetic aspects of DNA base pairing to divide the final product into its precursor 8-mers. This program compares all of the possible hybridizations (the act of two single-stranded oligonucleotides joining by hydrogen bond-mediated base pairing to become a double-stranded DNA molecule) of the 8-mers into which the target DNA molecule has been divided. There are many opportunities for error in the synthesis process, most of which are caused by improper hybridization of 8-mers to one another. The computer program is designed to minimize these errors by combining the 8-mers into small groups that are the most likely to produce the desired product, and the least likely to produce errors.

How the short oligos are assembled into longer DNA molecules: The groups of 8-mers are combined with the necessary reagents to allow DNA polymerase-based DNA synthesis. These include the appropriate buffers and nucleotides. The specifics of this process are contained in the 4-mer embodiment. Once the 8-mers have been converted into the desired product (e.g., 40-base-pair molecules), then these 40 base-pair products are themselves combined into subsequent polymerase-mediated reactions, in combinations dictated by the computer program. In this way, the reactions progress from converting groups of ten 8-mers into 40-base-pair molecules, then converting groups of 40 base-pair molecules into longer (e.g., 200-base-pair) molecules, and then finally converting these into the final, desired product.

Section 1: Use of odd-sized starting oligos—Referring now to FIG. 4, another embodiment of a system of creating long DNA sequences, e.g., 1-10 kilobases, from short oligos of length n (n-mers) of the present invention is illustrated. The system is designated generally by the reference numeral 400. The system of parallel synthesis 400 provides a process for making very long (greater than is possible with conventional phosphoramidite chemistry) DNA of user-defined sequence. The method begins by using computational techniques to break the desired sequence into fragments of defined size.

These n-base fragments are then arrayed in groups of n-base oligonucleotides and assembled into double-strand DNA molecules using DNA polymerase. The starting oligos may be of size n, where n is an odd number. The desired, hybridizing overlaps between oligos in the first thermocycle of PCR may be specified by the user. Table 1 gives a few examples of the overlap length, oligo length, and number of polymerized bases for several scenarios of starting oligo size and overlap in the first thermocycle, and the formula for computing these variables. The products of the reactions in the first tier of PCR reactions (each PCR reaction involves many thermocycles) are then combined, in as many steps as necessary, and assembled by polymerase into still-longer molecules, until the final desired product is assembled. The final product is then amplified using PCR.

The assembly process is substantially the same as the process called DNA shuffling. It is similar to PCR in that there is a template, a primer, a DNA polymerase, and the attendant nucleotides and buffers. It is dissimilar to PCR in that the primer and template are the same entities—the n-mers themselves. Following the parallel assembly process, the final product can be amplified by PCR. Any DNA polymerase commonly used for PCR can be used for this purpose.

The system 400 is similar to the system 300 described above and illustrated in FIG. 3; however, in the system 400, the starting oligos may be of odd length instead of even length. That is, in the system 300, the oligos, or n-mers, are of even length equal to n with a hybridizing overlap between complementary oligos of length n/2 in the first two thermocycles. In contrast, in the system 400, the length n may be odd, and the overlap length between hybridizing oligos may be specified by the user. Given a desired overlap $v_1$ in the first thermocycle and the length n of the starting oligos that are specified by the user, the length $l_c$ of oligonucleotides starting thermocycle c is computed by the formula: $l_c=n(c-1)+p_1$ for $c>1$, where $p_1=n-v_1$. The length $v_c$ of desired overlap between oligos in thermocycle c is given by $v_c=n(c-2)+p_1$ for $c>1$. The number $p_c$ of bases polymerized in thermocycle c is $p_c=n$ for $c>1$.

Figure 4:
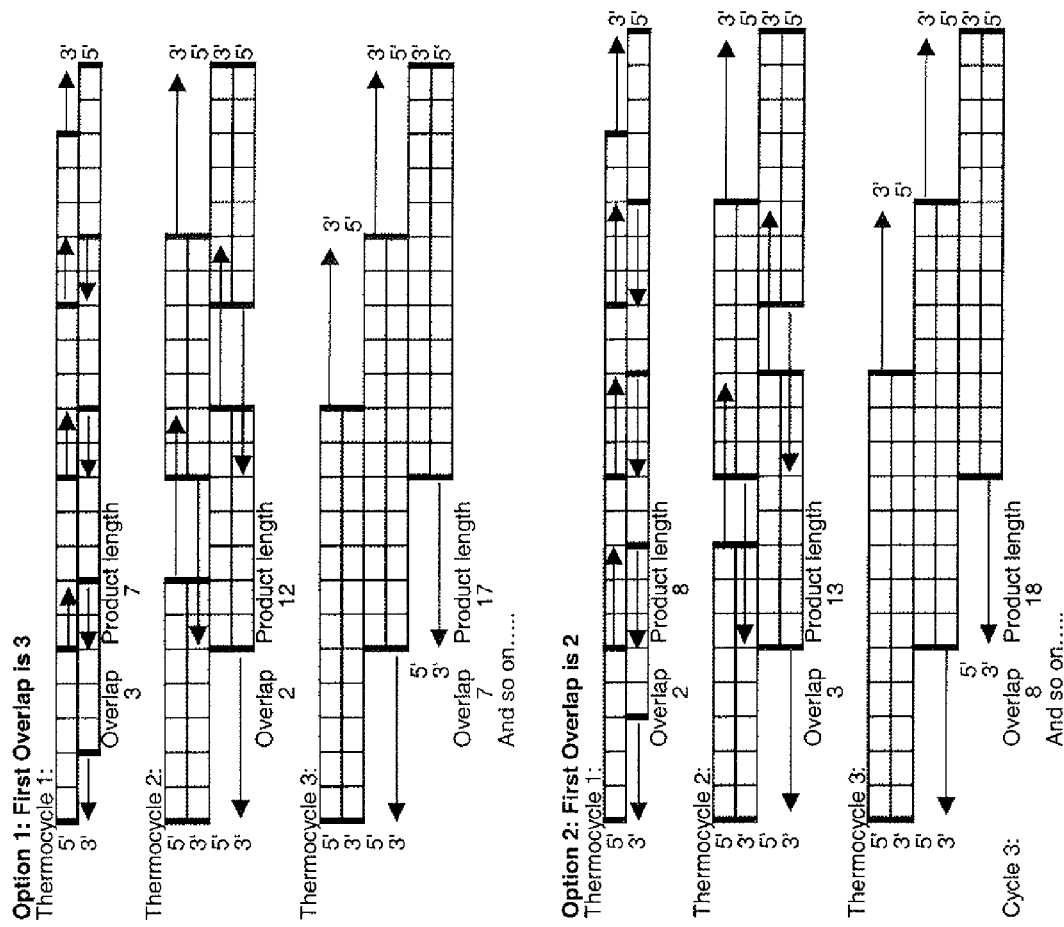
FIG. 4 illustrates another embodiment of a system of creating long DNA sequences, e.g., 1-10 kilobases, from short oligos of length n (n-mers) of the present invention.

FIG. 4 illustrates the first three thermocycles for the two scenarios starting with n=5 outlined in Table 1 below. Each yellow box indicates a nucleotide, and a series of yellow boxes represents an oligonucleotide, where the heavy black vertical lines indicate the ends of an oligonucleotide. The 5' and 3' ends of the plus and minus strands are labeled, and where nucleotides are in the same column (overlap vertically) and in the right orientation (5' to 3' on the top strand, and 3' to 5' on the bottom, from left to right), the desired hybridization occurs. Red arrows indicate polymerization (both the direction and the number of polymerized bases) from 3' ends during the specified thermocycle. In the first case, in which the first overlap $v_1=3$, polymerization extends each oligonucleotide by $p_1=2$ bases, and the length of the oligonucleotides starting the second thermocycle is 7 bases. In the second case, the first overlap $v_1=2$, polymerization extends each oligonucleotide by $p_1=3$ bases, and the length of the oligonucleotides starting the second thermocycle is 8 bases. These are merely two examples, and any other values of n and $v_1$ specified by the user may be used.

Table 1, below, shows: Length $l_c$ of oligonucleotides starting thermocycle c, length $v_c$ of desired overlap, and number $p_c$ of bases polymerized in thermocycle c. The general formula for each is: $l_c=n(c-1)+p_1$ for c>1, $v_c=n(c-2)+p_1$ for c>1, and $p_c=n$ for c>1. The desired overlap in the first thermocycle ($v_1$) and the length n of the starting oligos are specified by the user, and the number of bases polymerized in the first thermocycle is $p_1=n-v_1$.

TABLE 1

| Thermocycle "c" | length "$l_c$" of oligonucleotides at start of thermocycle | length "$v_c$" of overlap for desired hybridizations | number "$p_c$" of bases polymerized in thermocycle c |
|---|---|---|---|
| Starting oligo size n = 4 | | | |
| 1 | 4  | 2  | 2 |
| 2 | 6  | 2  | 4 |
| 3 | 10 | 6  | 4 |
| 4 | 14 | 10 | 4 |
| 5 | 18 | 14 | 4 |
| Starting oligo size n = 5 | | | |
| 1 | 5  | 3  | 2 |
| 2 | 7  | 2  | 5 |
| 3 | 12 | 7  | 5 |
| 4 | 17 | 12 | 5 |
| 5 | 22 | 17 | 5 |
| 1 | 5  | 2  | 3 |
| 2 | 8  | 3  | 5 |
| 3 | 13 | 8  | 5 |
| 4 | 18 | 13 | 5 |
| 5 | 23 | 18 | 5 |

Figure 5:
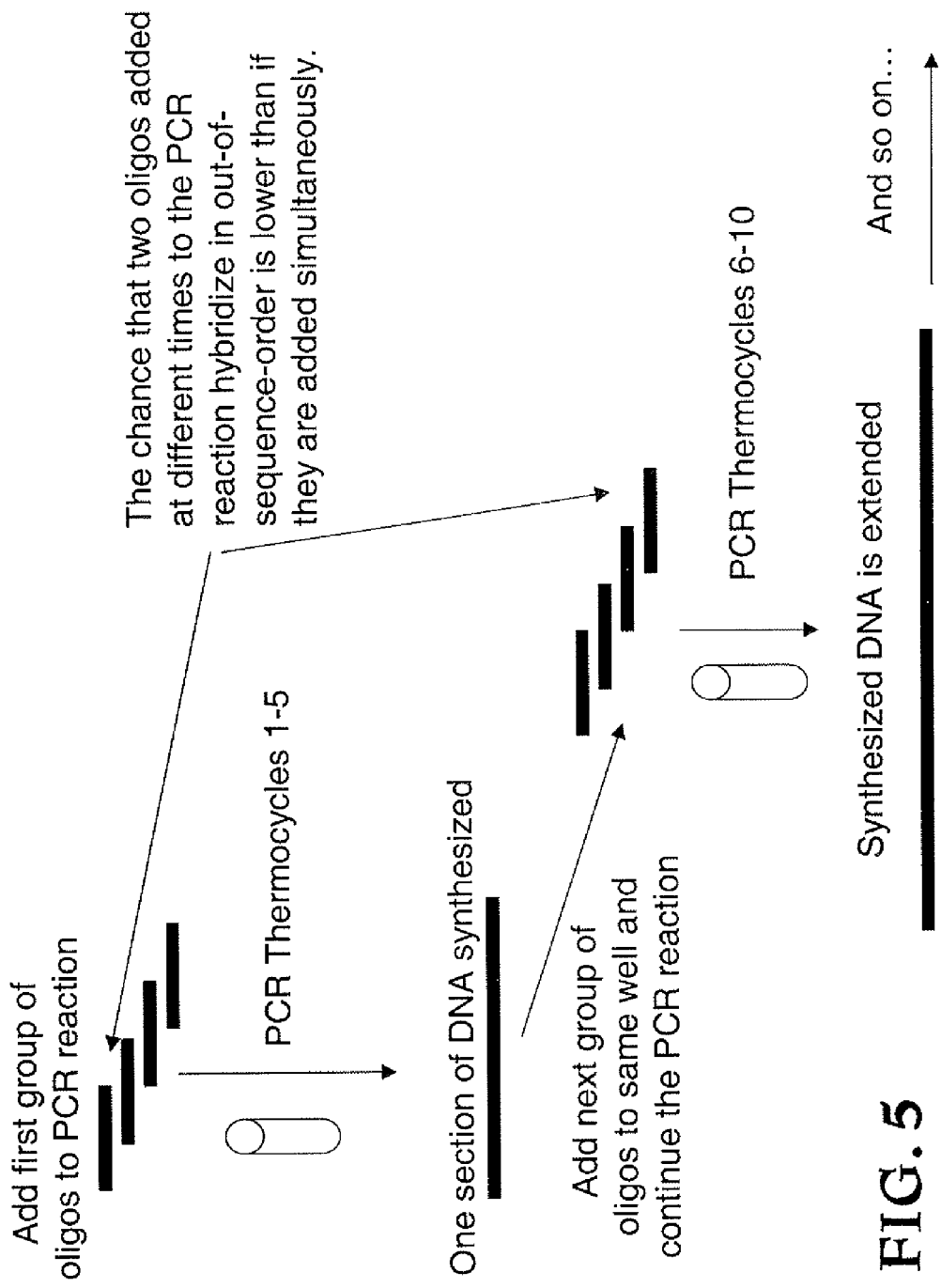
FIG. 5 illustrates another embodiment of a system of creating long DNA sequences, e.g., 1-10 kilobases, from short oligos of length n (n-mers) of the present invention

Section 2: Gradual addition of oligos to PCR reactions—Referring now to FIG. 5, another embodiment of a system of creating long DNA sequences, e.g., 1-10 kilobases, from short oligos of length n (n-mers) of the present invention is illustrated. The system is designated generally by the reference numeral 500. The system of parallel synthesis 500 provides a process for making very long (greater than is possible with conventional phosphoramidite chemistry) DNA of user-defined sequence. The method begins by using computational techniques to break the desired sequence into fragments of defined size.

These n-base fragments are then arrayed in groups of n-base oligonucleotides and assembled into double-strand DNA molecules using DNA polymerase. The groups of oligos are separated temporally. That is, oligos are added gradually, in sequence order or other order that is predicted (computationally) to minimize errors, over time through the many thermocycles of hybridization and polymerization. The products of these reactions are then combined, in as many steps as necessary, and assembled by polymerase into still-longer molecules, until the final desired product is assembled. The final product is then amplified using PCR.

The assembly process is substantially the same as the process called DNA shuffling. It is similar to PCR in that there is a template, a primer, a DNA polymerase, and the attendant nucleotides and buffers. It is dissimilar to PCR in that the primer and template are the same entities—the n-mers themselves. Following the parallel assembly process, the final product can be amplified by PCR. Any DNA polymerase commonly used for PCR can be used for this purpose.

The system 500 is similar to the system 300 described above and illustrated in FIG. 3; however, in the system 500, instead of, or in addition to, separating groups of oligos spatially into different wells, the groups of oligos are separated temporally. That is, oligos are added gradually, in sequence order or other order that is predicted (computationally) to minimize errors, over time through the many thermocycles of hybridization and polymerization. For example, the first four oligo sequences might be added initially, five thermocycles completed, and then another four oligo sequences added corresponding to sequence further along the DNA chain, and so on, for many (e.g., 30) thermocycles. By gradually adding the building blocks of the sequence in an order predicted computationally to minimize incorrect hybridizations, the probability may be increased that each successive oligo will bind in the correct order to the sticky tail of the growing chain(s).

In DNA-polymerase-based synthesis, the error rate can be substantial. Applicants' technique to address this problem described in connection with FIGS. 2 and 3 is to subdivide the oligos that will be run through DNA-polymerase-based synthesis into separate wells, based on the minimization of incorrect hybridizations. In situations where incorrect but perfect hybridization would occur, those oligos are put into separate wells. The products of each of these wells are then mixed to create longer DNA via polymerase-based extension. In the system 500, Applicants add the oligos gradually, over multiple thermocycles, to each well, thus further reducing the likelihood that an oligo at one end of the sequence will bind to one that is distant in the desired sequence (i.e., out of order). This is because the oligos at one end of the sequence would already be assembled into a longer chain by the time that oligos further along the desired chain are introduced into the reaction. This technique enables the use of fewer wells when temporal separation of the oligos competing for hybridization, instead of or in addition to spatial separation, is employed.

Section 3: Use of oligos from overlapping, multiple reading frames within the same PCR reaction—Referring now to FIG. 6, another embodiment of a system of creating long DNA sequences, e.g., 1-10 kilobases, from short oligos of length n (n-mers) of the present invention is illustrated. The system is designated generally by the reference numeral 600. The system of parallel synthesis 600 provides a process for making very long (greater than is possible with conventional phosphoramidite chemistry) DNA of user-defined sequence. The method begins by using computational techniques to break the desired sequence into fragments of defined size.

Figure 6:
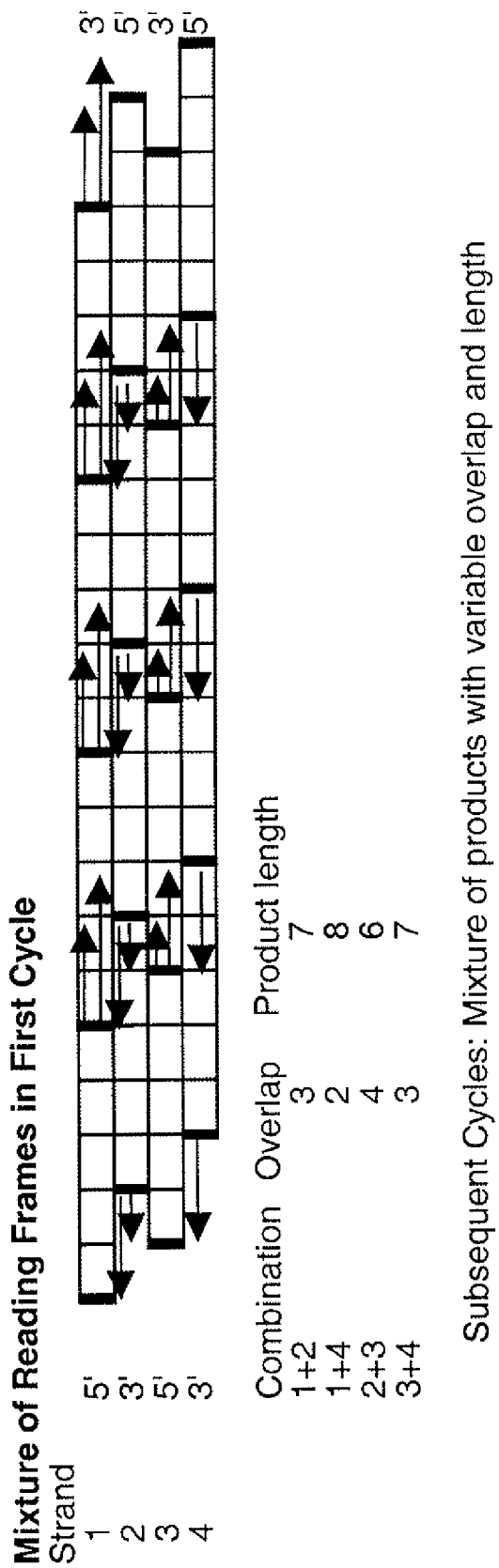
FIG. 6 illustrates another embodiment of a system of creating long DNA sequences, e.g., 1-10 kilobases, from short oligos of length n (n-mers) of the present invention

These n-base fragments are then arrayed in groups of n-base oligonucleotides and assembled into double-strand DNA molecules using DNA polymerase. The starting oligos may be of size n, where n is an even or an odd number. The desired, hybridizing overlaps between oligos in the first thermocycle of PCR may be of different lengths depending on the particular pair of oligos that are hybridizing. FIG. 6 illustrates how the same sequence of DNA may be spanned by multiple oligos of length n, each frame-shifted from one another, and combined in the same well (i.e. the same PCR reaction). Thus, a given sequence would be represented more than once by oligos in different reading frames that will hybridize with different overlap lengths. Desired hybridizations between complementary oligos in the correct 5' and 3' orientations (an oligo corresponding to the plus strand with an oligo corresponding to the minus strand) may occur in more than one way. Desired overlaps may be of multiple, different lengths, depending on the pair of oligos hybridizing. For example, one such scenario is pictured in FIG. 5 for pentamers, in which oligos from two reading frames are tiled in the same well, and desired overlaps in the first thermocycle range from 2 to 4 bases.

The products of the reactions in the first tier of PCR reactions (each PCR reaction involves many thermocycles) are then combined, in as many steps as necessary, and assembled by polymerase into still-longer molecules, until the final desired product is assembled. The final product is then amplified using PCR.

The assembly process is substantially the same as the process called DNA shuffling. It is similar to PCR in that there is a template, a primer, a DNA polymerase, and the attendant nucleotides and buffers. It is dissimilar to PCR in that the primer and template are the same entities—the n-mers themselves. Following the parallel assembly process, the final product can be amplified by PCR. Any DNA polymerase commonly used for PCR can be used for this purpose.

The system 600 is similar to the system 300 described above and illustrated in FIG. 3; however, in the system 600, the starting oligos may be in multiple different reading frames spanning the same desired DNA sequence to be synthesized. That is, in the system 300, the oligos are all in the same reading frame in a given PCR reaction (i.e., in a given well in which the PCR reaction occurs). In contrast, in the system 600, the oligos may be in more than one reading frame, shifted by some number of bases. The oligos span the same total length and sequence, but may hybridize together in more than one possible desired interaction.

FIG. 6 illustrates one possible scenario of using oligos from multiple reading frames. The starting oligos are of size n=5, and are in two reading frames on both the plus and minus strands. Each yellow box indicates a nucleotide, and a series of yellow boxes represents an oligonucleotide, where the heavy black vertical lines indicate the ends of an oligonucleotide. The 5' and 3' ends of the plus and minus strands are labeled, and where nucleotides are in the same column (overlap vertically) and in the right orientation (5' to 3' on the top strand, and 3' to 5' on the bottom, from left to right), the desired hybridization occurs. Red arrows indicate polymerization (both the direction and the number of polymerized bases) from 3' ends during the specified thermocycle. Strands are numbered 1-4 for discussion purposes. In the first thermocycle, if strands 1 and 2 hybridize, the desired overlap is 3 bases, and polymerization extends the oligos by 2 bases from the 3' end, leading to products of length 7 bases. If strands 1 and 4 combine, the desired overlap is two bases, polymerization extends by 3 bases, and the product is 8 bases. If strands 2 and 3 hybridize, the overlap is 4 bases, extension is 1 base, and product is 6 bases. Hybridization of oligos from strands 3 and 4 with a desired overlap of 3 bases leads to extension by 2 bases and 7 base products. The products from the first thermocycle, of the lengths given above, may hybridize in a number of combinations and desired overlap lengths in subsequent thermocycles.

Section 4: Use of starting oligos of different lengths— Referring now to FIG. 7, another embodiment of a system of creating long DNA sequences, e.g., 1-10 kilobases, from short oligos of length n, n+1, n+2, etc. of the present invention is illustrated. The system is designated generally by the reference numeral 700. The system of parallel synthesis 700 provides a process for making very long (greater than is possible with conventional phosphoramidite chemistry) DNA of user-defined sequence. The method begins by using computational techniques to break the desired sequence into fragments of different sizes in the first tier of the parallel pyramid synthesis plan. Instead of using oligos only of size n, oligos of size n, n+1, n+2, etc. may be combined. These longer oligos would be used only for sequence regions in which synthesis using oligos of size n would be likely to result in sequence errors due to factors such as, but not limited to, self complementarity or hetergeneous DNA melting temperatures. Using longer oligos for these problematic regions would reduce the probability of incorrect hybridizations. It is possible to predict a number of these regions in advance, and have on hand a library of longer oligos to synthesize such sequence.

Figure 7:
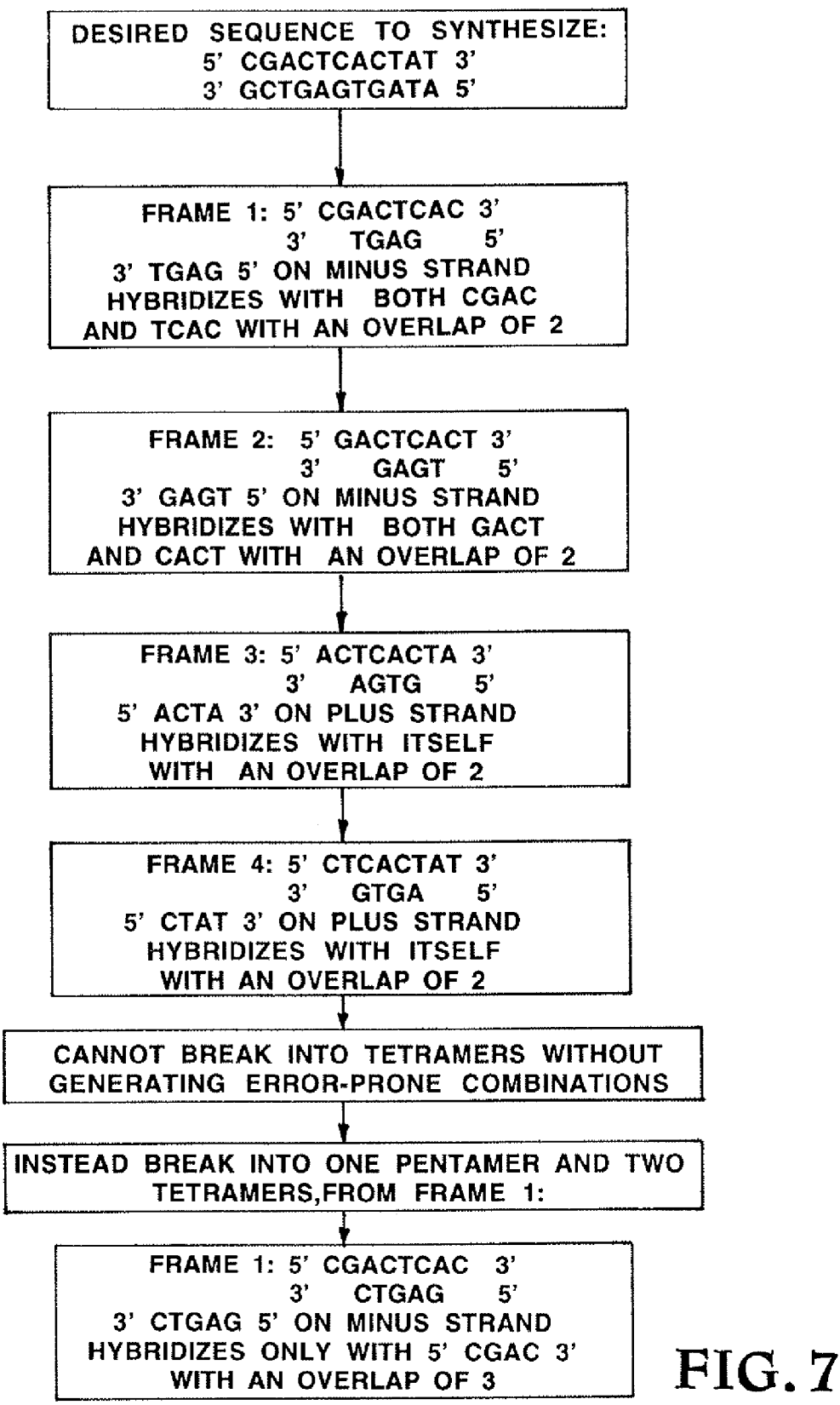
FIG. 7 illustrates another embodiment of a system of creating long DNA sequences, e.g., 1-10 kilobases, from short oligos of length n, n+1, n+2, etc. of the present invention (SEQ ID NO: 1).

These fragments of multiple sizes are then arrayed in groups of oligonucleotides and assembled into double-strand DNA molecules using DNA polymerase. The starting oligos may be of size n, n+1, n+2, etc. The desired, hybridizing overlaps between oligos in the first thermocycle of PCR may be of different lengths depending on the lengths of the pair of oligos that are hybridizing. FIG. 7 illustrates how a DNA sequence may be spanned by oligos of multiple lengths. Hybridizations occur between complementary oligos in the correct 5' and 3' orientations (an oligo corresponding to the plus strand with an oligo corresponding to the minus strand). In this formulation, many of the oligos are of size n, but where it is not possible to divide a region of the DNA sequence into starting oligos of size n without being forced to combine some oligos that are likely to hybridize incorrectly (that will yield an undesired DNA sequence after extension), then oligos of length greater than n may be used. Error prone combinations may result from self-complementary sequence, repetitive sequence, incompatible melting temperatures, or other situations in which the likelihood of incorrect hybridization approaches or exceeds that of the desired hybridization. In some cases, it may be possible to pre-specify problematic DNA sequences for synthesis with oligos of length n, and to have on hand oligos of length n+1, n+2, etc. that are unlikely to hybridize in error-prone combinations for these particular DNA sequences. Then, the longer oligos may be used to synthesize these problematic regions, and the standard oligos of size n may be used to synthesize the remainder of the DNA sequence.

The products of the reactions in the first tier of PCR reactions (each PCR reaction involves many thermocycles) are then combined, in as many steps as necessary, and assembled by polymerase into still-longer molecules, until the final desired product is assembled. The final product is then amplified using PCR.

The assembly process is substantially the same as the process called DNA shuffling. It is similar to PCR in that there is a template, a primer, a DNA polymerase, and the attendant nucleotides and buffers. It is dissimilar to PCR in that the primer and template are the same entities—the oligos themselves. Following the parallel assembly process, the final product can be amplified by PCR. Any DNA polymerase commonly used for PCR can be used for this purpose.

The system 700 is similar to the system 300 described above and illustrated in FIG. 3; however, in the system 700, the starting oligos may be of multiple different lengths. That is, in the system 300, the starting oligos are all of the same size n in a given PCR reaction (i.e., in a given well in which the PCR reaction occurs). In contrast, in the system 700, the oligos may be different lengths.

FIG. 7 illustrates one possible scenario of using oligos from multiple reading frames for synthesizing the sequence 5' CGACTCACTAT 3' (SEQ ID NO: 1). If the starting oligos are all of size n=4, every possible combination of tetramers in the four possible reading frames will result in error-prone combinations in which undesired hybridizations are as likely as desired hybridizations. However, if one pentamer is used in combination with the remaining tetramers, it is possible to generate a group of oligos that are not likely to hybridize in undesired combinations.

It is to be understood that the invention is not limited to the particular forms disclosed. Rather, the invention covers all modifications, equivalents, and alternatives falling within the spirit and scope of the invention as defined by the claims.

The invention claimed is:

1. A method of fabricating a DNA molecule from n-base oligonucleotides that are assembled into double-strand DNA molecules using DNA polymerase, comprising the steps of:

preselecting a multiplicity of DNA sequence segments that will comprise said DNA molecule, wherein said multiplicity of DNA sequence segments are of size n, where n is an odd number, wherein said multiplicity of DNA sequence segments comprises oligos in multiple reading frames, separating said multiplicity of DNA sequence segments temporally, thereby providing a multiplicity of temporally separated DNA sequence segments, and combining said multiplicity of temporally separated DNA sequence segments with at least one polymerase enzyme with overlaps between said temporally separated DNA sequence segments of size n, where n is an odd number, wherein said multiplicity of temporally separated DNA sequence segments join to produce said DNA molecule.

* * * * *

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
cgactcacta t                                                        11
```